United States Patent [19]

Matsumoto

[11] Patent Number: 5,516,565
[45] Date of Patent: May 14, 1996

[54] HYDROXYALKANOATE POLYMER COMPOSITION

[75] Inventor: Atsushi Matsumoto, Kanagawa, Japan

[73] Assignee: Terumo Kabushiki Kaisha, Tokyo, Japan

[21] Appl. No.: 257,041

[22] Filed: Jun. 8, 1994

[30] Foreign Application Priority Data

Jun. 10, 1993 [JP] Japan .................. 5-138744

[51] Int. Cl.⁶ .................................................. C08L 67/04
[52] U.S. Cl. .................. 428/35.7; 428/36.9; 428/36.92; 523/105; 523/111; 523/113; 524/240; 524/599; 525/450
[58] Field of Search .................. 525/450; 523/105, 523/111, 113; 524/186, 288, 599, 240; 428/35.7, 36.92, 36.9

[56] References Cited

U.S. PATENT DOCUMENTS

| | | |
|---|---|---|
| 4,393,167 | 11/1981 | Holmes et al. . |
| 4,876,331 | 8/1988 | Doi . |
| 4,910,145 | 6/1989 | Holmes et al. . |
| 5,061,743 | 5/1990 | Herring et al. . |

FOREIGN PATENT DOCUMENTS

| | | |
|---|---|---|
| 0446852 | 9/1991 | European Pat. Off. . |
| 4102170 | 8/1992 | Germany . |
| 52-5935 | 2/1977 | Japan . |
| 53-117044 | 10/1978 | Japan . |
| 57-150393 | 9/1982 | Japan . |
| 57-174094 | 10/1982 | Japan . |
| 59-220192 | 12/1984 | Japan . |
| 60-145097 | 7/1985 | Japan . |
| 64-48821 | 2/1989 | Japan . |
| 3-24151 | 2/1991 | Japan . |
| WO01/19759 | 12/1991 | WIPO . |

OTHER PUBLICATIONS

Miller et al., On the biodegradation of poly–β–hydroxybutyrate (PHB) homopolymer and poly–β–hydroxybutyrate–hydroxyvalerate copolymers, 1987, pp. 129–137.

Saito et al, In vivo and in vitro degradation of poly(3–hydroxybutyrate) in rat, 1991, pp. 309–312.

Malm et al., Prevention of postoperative pericardial adhesions by closure of the pericardium with absorbable polymer patches, 1992, pp. 600–607.

Primary Examiner—Patricia A. Short
Attorney, Agent, or Firm—Burns, Doane, Swecker & Mathis

[57] ABSTRACT

There is provided a highly biodegradable resin composition comprising a hydroxyalkanoate polymer and a crystallization nucleating agent. The resin composition may typically comprise a hydroxybutyrate homopolymer or a hydroxybutyrate-hydroxyvalerate copolymer and an aromatic amino acid. There is also provided a device prepared by using such a resin composition. The resin composition of the invention is capable of undergoing a crystallization at a high speed to provide the article molded therefrom with improved properties. The resin composition is also highly degradable in an animal body or in the environment.

9 Claims, 1 Drawing Sheet

HYDROXYALKANOATE POLYMER COMPOSITION

BACKGROUND OF THE INVENTION

This invention relates to a hydroxyalkanoate polymer composition, and more specifically, to a resin composition comprising a hydroxybutyrate homopolymer or a hydroxybutyrate-hydroxyvalerate copolymer. This invention also relates to a device fabricated from such a resin composition.

Hydroxybutyrate homopolymer and a hydroxybutyrate-hydroxyvalerate copolymer are formed in a bacteria or other microorganisms for their energy source, and these polymers are biodegradable thermoplastic polyesters which are decomposed and digested by various microorganisms commonly present in soil. It is also known that these polymers are degradable in an organism without stimulating any hazardous reaction. For example, N. D. Miller and D. F. Williams disclose that hydroxybutyrate homopolymer and a hydroxybutyrate-hydroxyvalerate copolymer are decomposed in an organism through a hydrolyric process and an enzymatic process. See Biomaterial, vol. 8, page 129, 1987. T. Saito et al. also disclose similar results. See Biomaterial, vol. 12, page 309, 1991. There is also reported in J. Thorac. Cardiovasc. Surg., vol. 104, page 600, 1992 that use of a hydroxybutyrate homopolymer for an artificial heart membrane resulted in a favorable tissue response.

Hydroxybutyrate homopolymer was discovered several decades ago. However, it was not put into a practical use until quite recently since its extraction from the bacteria and subsequent purification were quite difficult, and since its decomposition point (183° C.) and melting point (180° C.) were too close to enable a uniform molding. Backed by recent heightening in the interest in environmental issues, there were developed various techniques for copolymerizing the hydroxybutyrate with another hydroxyalkanoate (Japanese Patent Application Kokai (unexamined laid open) No. 57(1982)-150393 and 59(1984)-220192) as well as purification processes (Japanese Patent Application Kokai Nos. 57(1982)-174094 and 60(1980)-145097) to enable supply of lower melting materials with a relatively improved moldability. Hydroxybutyrate homopolymer inherently suffers from a lower crystallization speed compared to other commonly used synthetic materials, and in particular, hydroxybutyrate-hydroxyvalerate copolymers suffer from a decrease in crystallization speed with an increase in the hydroxyvalerate content. In the case of injection molding, an excessively low crystallization speed would lead to a difficulty in temperature control upon solidification of the resin in the mold to result in molding failures due to an insufficient solidification or "sinkmarks", and an unduly prolonged molding cycle would lead to an increased production cost. In the case of extrusion molding, insufficiently crystallized articles would adhere to each other even at room temperature and consequently, such molded articles would be quite inconvenient to handle. Furthermore, low crystallization speed is likely to induce a growth of large spherulites to result in brittle molded articles.

In view of such situation, a crystallization nucleating agent is generally incorporated in such a resin to thereby improve precision of the molded articles upon injection molding or extrusion, to provide a mirror surface with the molded articles, and to improve various other properties of the molded articles. For example, there is described in Japanese Patent Publication (examined laid open) No. 52(1977)-5935 that an addition of dibenzalsorbit to polypropylene as a nucleating agent upon melting and molding of the resin is effective in decreasing shrinkage upon molding and in preventing "sinkmarks" of the molded articles. There is also described in Japanese Patent Application Kokai No. 3(1991)-24151 that an addition of a metal compound in combination with organic sulfonic acid or organic phosphinic acid to a hydroxyalkanoate polymer would result in a high crystallization and a decreased brittleness of the molded articles.

Boron nitride is generally known to be a nucleating agent for resins, and boron nitride proved to be a good nucleating agent for the hydroxyalkanoate polymer of the present invention. However, boron nitride is less likely to undergo degradation under natural environment, and consequently, the boron nitride used as the nucleating agent is likely to remain undecomposed even after the degradation of the resin composition. In particular, when boron nitride is incorporated into various devices to be implanted in a living body, which is designed to be decomposed and absorbed in the living body, the boron nitride remained unabsorbed may generate a chronic inflammation or a cancer. The process of Japanese Patent Application Kokai No. 3(1991)-24151, wherein a polyhydroxyalkanoate is admixed with a combination of a metal compound and organic phosphonic acid or organic phosphinic acid, also requires an adequate selection of the materials which are nontoxic to a living body. Such a selection should require considerable experimentation since a combination of two compounds should be evaluated for their toxicity and nucleating effects.

SUMMARY OF THE INVENTION

An object of the present invention is to provide a hydroxyalkanoate polymer composition free from the defects of the conventional hydroxyalkanoate polymer composition including the slow crystallization which led to "sinkmarks" and other molding failures of the molded articles due to an insufficient solidification as well as brittleness of the molded product.

Another object of the present invention is to provide a non-toxic hydroxyalkanoate polymer composition which would be readily resorved or metabolized in a living body after its degradation to thereby enable production of biodegradable molded articles and devices.

According to the present invention, there is provided a resin composition comprising a hydroxyalkanoate polymer; and a crystallization nucleating agent which is capable of being decomposed or metabolized in an animal or in the environment at a level equivalent to or higher than that of the hydroxyalkanoate polymer.

The hydroxyalkanoate polymer may preferably be a polymer having weight average molecular weight of 1,000–1,000,000 represented by the recurring unit of the formula (I):

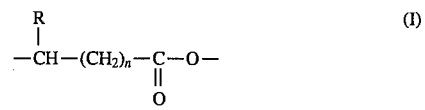

wherein R is hydrogen or an alkyl group having 1 to 4 carbon atoms; n is an integer of from 1 to 8.

The hydroxyalkanoate polymer may preferably be a hydroxybutyrate homopolymer or a hydroxybutyrate-hydroxyvalerate copolymer having the amount of the hydroxyvalerate of from 0 to 30% (w/w).

The crystallization nucleating agent may be an aromatic amino acid, and preferably, tyrosine or phenylalanine.

There is also provided by the present invention a method for producing the resin composition of the invention comprising the steps of dissolving the hydroxyalkanoate polymer in a solvent to produce a solution; adding 0.1 to 10 parts by weight based on 100 parts by weight of the hydroxyalkanoate polymer of the crystallization nucleating agent to the solution and thoroughly dispersing the nucleating agent in the solution to produce a fully dispersed dispersion; and casting the dispersion on a glass plate.

Furthermore, there is provided by the present invention, a device fabricated by using the resin composition of the present invention such as infusion system, blood transfusion system, blood circuit, catheter, blood bag, infusion bag, dialysis bag, perintestinal nutrient bag, suture, mesh, patch, pledger, prosthesis, staple, clip, coalescence preventing film, or implant material or screw used for its fixing.

DESCRIPTION OF THE INVENTION

Figure 1:
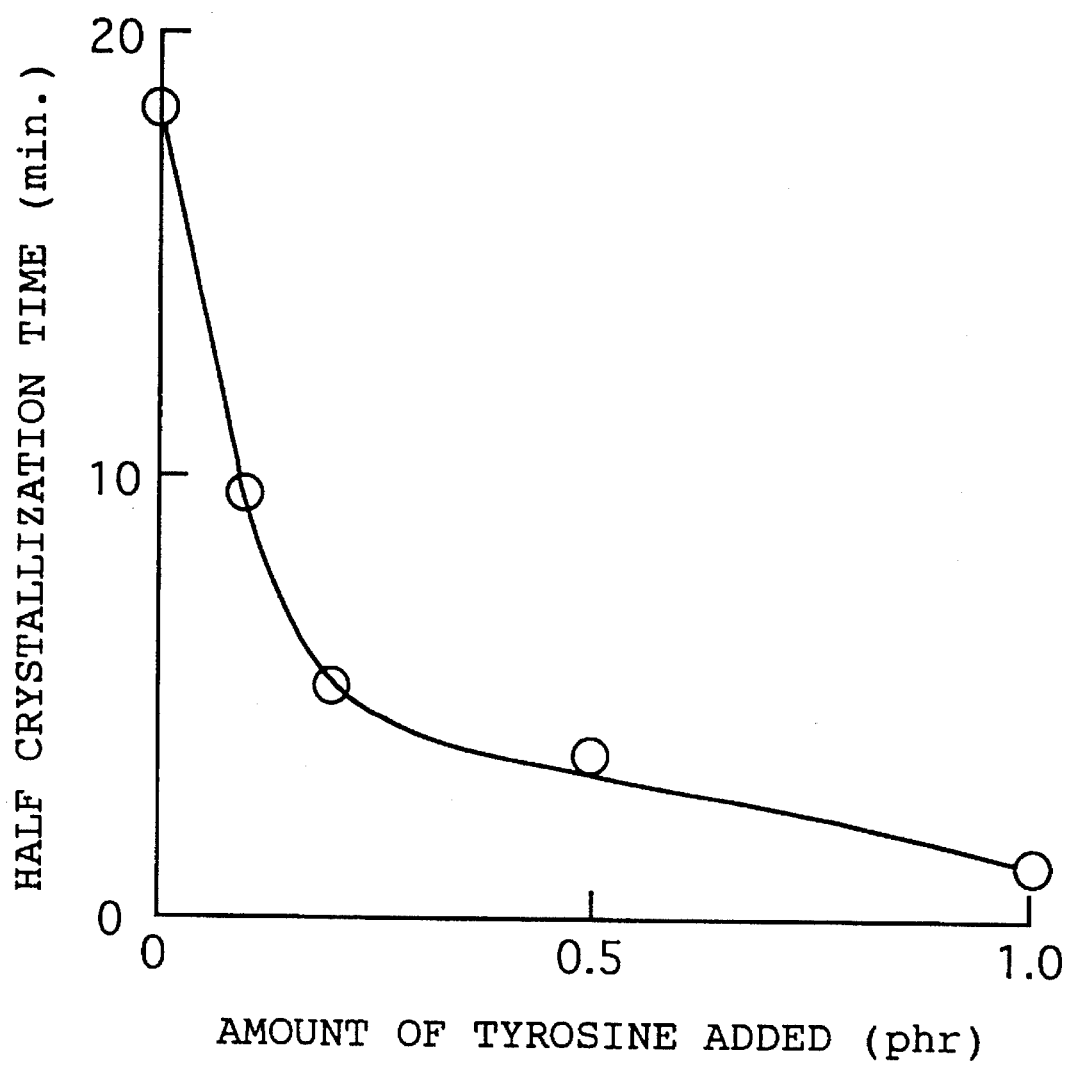
FIG. 1 is a view showing half crystallization time of the present composition in relation to the amount of tyrosine added.

The hydroxyalkanoate polymer used in the present invention may preferably be a polymer having weight average molecular weight of 1,000–1,000,000 represented by the recurring unit of the following formula (I):

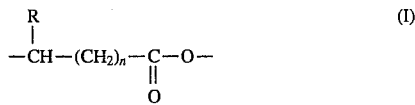

wherein R is hydrogen or an alkyl group having 1 to 4 carbon atoms; n is an integer of from 1 to 8. R may preferably be methyl or ethyl group; and the polymer used in the present invention may preferably be a copolymer of the structural units wherein R is methyl and ethyl, respectively. n may preferably be an integer of from 1 to 2.

The hydroxyalkanoate polymer used in the present invention may preferably be a hydroxybutyrate homopolymer which is a polymer of the structural unit wherein R is methyl group and n is 1; or a hydroxybutyrate-hydroxyvalerate copolymer which is a copolymer of the hydroxybutyrate unit and a hydroxyvalerate unit wherein R is ethyl and n is 1. Weight average molecular weight of the polymer is from about 1,000 to about 1,000,000, and preferably, from about 100,000 to 1,000,000. The copolymer may preferably contain the hydroxyvalerate in an amount of from 0 to 30% (w/w) since the polymer containing such units in the above-defined range would have a melting point of from 140° to 180° C. to enable a convenient molding.

The hydroxyalkanoate polymer used in the present invention may be produced by various conventional methods such as a fermentation using a microorganism adapted for producing such a polymer, or a chemical synthesis.

Various microorganisms known to produce such a polymer may be used in the present invention. For example, the hydroxyatkanoate polymer of the present invention may be produced by incubating hydrogen bacterium, *alkaligenes eutrophus* H16 ATCC 17699 in a phosphate buffer solution medium, pH 7.5 having added thereto fructose and minerals at 30° C. for 2 days to allow for the target poly(3-hydroxybutyrate) to accumulate in the bacteria, and extracting the thus accumulated polymer in chloroform; or by repeating the above-described procedure except for the addition of valeric acid instead of the fructose to thereby obtain a (3-hydroxybutyrate)-(3-hydroxyvalerate) copolymer; or by repeating the above-described procedure except for the addition of γ-butyrolactone instead of the fructose to thereby obtain a (3-hydroxybutyrate)-(4-hydroxybutyrate) copolymer.

Alternatively, 3-hydroxybutyrate, 3-hydroxybutyrate chloride, 4-hydroxyvalerate, β-butyrolactone, γ-butyrolactone, β-valerolactone, or the like may be subjected to a polycondensation or ring opening polymerization to synthesize a poly(3-hydroxyalkanoate), a poly(4-hydroxyalkanoate), or a copolymer thereof.

In the present invention, commercially available hydroxyalkanoate polymers may also be employed, for example, those available from Aldrich and Polyscience.

The hydroxyalkanoate polymers as described above are known to be highly biodegradable since they are completely decomposed by microorganisms or compounds secreted from microorganisms.

The resin composition of the present invention comprises the hydroxyalkanoate polymer as described above as its main component. The resin composition of the present invention also comprises a crystallization nucleating agent which would be decomposed or metabolized in or excreted from an animal body, and which would be decomposed in the environment at a level equivalent to or higher than the hydroxyalkanoate polymer.

Japanese Patent Application Kokai No. 53(1978)-117044 describes that an additive which is capable of gelling a resin has a nucleating effect, but the nucleating effect may show a complicated behavior in accordance with the type of the target resin and the nature of the nucleating agent. In view of such a situation, inventors of the present invention have paid attention to amino acids which are always present in an organism and which can be safely and readily metabolized, and investigated their nucleating effects to find that aromatic amino acids, especially tyrosine, may serve an excellent nucleating agent for the hydroxyalkanoate polymer showing a crystallization promoting effect higher than that of boron nitride.

It should be noted that the term, aromatic amino acids used herein designates an amino acid which has an aromatic ring as its side chain. Exemplary aromatic amino acids include tyrosine and phenylalanine as being the preferred.

The hydroxyalkanoate polymer composition of the present invention may contain at least 0.1 part by weight, and preferably, from 0.1 to 10 part by weight, more preferably from 0.1 to 1 part by weight of the nucleating aromatic amino acid per 100 parts by weight of the main component hydroxyalkanoate polymer.

The articles molded from the hydroxyalkanoate polymer composition of the present invention are sufficiently solidified to show no "sinkmarks" or other molding failures, such articles would also show a low brittleness, and should not adhere to each other to cause blocking, since such articles have undergone a crystallization at a high speed and to a sufficient degree.

In addition to the critical components as described above, the hydroxyalkanoate polymer composition of the present invention may optionally contain various additional components in an amount that would not adversely affect the advantageous features of the present invention.

The process for producing the hydroxyalkanoate polymer composition of the present invention is not limited to any particular process. In a typical process, a hydroxyalkanoate polymer is first dissolved in a solvent which may preferably be chloroform, methylene chloride, 1,2-dichloroethane, or dioxane; and to the solution is added from 0.1 to 10 parts by weight, and preferably, from 0.1 to 1 parts by weight per 100 parts by weight of the hydroxyalkanoate polymer of a crystallization nucleating agent which may preferably be an aromatic amino acid, which is thoroughly dispersed in the solution by such means as ultrasonication, and the like. The solvent may be removed from the finished article by elevating the temperature or by reducing the pressure, or alternatively, by allowing the finished article to stand for a while.

The medical device of the present invention is fabricated by using the hydroxyalkanoate polymer composition as described above or such a resin composition combined with another material.

The medical device which may be fabricated by using the hydroxyalkanoate polymer composition of the present invention is not limited to any particular type, and any medical device which had been fabricated from a conventional flexible material such as an elastomer, a rubber, a resin, or the like may be fabricated by using the resin composition of the present invention.

The medical device may have a non-limited configuration such as cylinder or tube, bag, box, column, cone, film or sheet, filament or thread, woven or nonwoven fabric, or the like.

Exemplary medical devices which may be fabricated by using the hydroxyalkanoate polymer composition of the present invention include blood transfusion system, infusion system, tube in blood circuit, connection tube, connector, manifold, instillation cylinder, multiple manifold, plug;

blood bag, infusion bag, urinary bag, dialysis bag, perintestinal nutrient bag, and other liquid bags;

urinary catheter, stomach tube catheter, balloon catheter, and other catheters;

suture, mesh, patch, pledger, coalescence preventing film, prosthesis, and other articles of thread, fabric, and sheet configuration;

staple, clip, implant material and screw used for its fixture, and other molded articles.

In view of the high biodegradability of the hydroxyalkanoate polymer composition of the present invention, it would be most suitable to use the resin material of the invention for a disposable medical device or a medical device which remains in the living body such as a fixture of an implant material.

It should be noted that the medical device of the present invention does not necessary comprise the hydroxyalkanoate polymer composition of the present invention as its only material. In the case of a balloon catheter, for example, the resin composition of the present invention may be used for either the balloon or the shaft portion of the catheter, and other materials can be used for the remaining part of the catheter. In the case of a liquid bag, the resin composition of the present invention may be used for fabricating the bag portion, and the remaining connector portion may be fabricated from conventional resins.

The hydroxyalkanoate polymer composition of the present invention may also be used for producing a laminate with a conventional resin.

The hydroxyalkanoate polymer composition of the present invention is thermoplastic in its nature. Therefore, in fabricating the medical device of the present invention of tubular, bag, or other configuration, any conventional process used for conventional thermoplastic resins may be employed in accordance with the configuration and the usage of the device and the installation used for the production. Such conventional processes include extrusion, injection molding, vacuum molding, and press molding, and in the case of a staple, for example, it can be fabricated by injection molding.

Similarly, for fabricating the medical device of the present invention with a filament configuration, any process used for fabricating an article of such a configuration from a conventional thermoplastic resin may be employed. An exemplary such process is a monofilament or a multifilament extrusion from an extruder at a cylinder and die temperature about 5° to 20° C. higher than the melting point of the resin composition extruded from the extruder.

The thus extruded filament may not have a strength sufficient for such an article as a suture, and in such a case, the filament may be oriented by a suitable process such as stretching of the extruded filament in an amorphous state in machine direction at a temperature between the glass transition temperature, Tg and the melting point, Tm of the resin composition for orientation, followed by crystallization. The thus oriented filament should have an improved strength.

The thus produced filament may be produced into a knitted thread, a woven fabric or a nonwoven fabric by any suitable process by any conventional process using a knitting or weaving machine. A suture, mesh, patch, pledget, and the like may be readily produced by such a process.

In addition to the extrusion process as mentioned above, a filamentous article may be produced by a so-called wet spinning wherein the resin composition is dissolved in a good solvent such as chloroform or 1,2-dichloroethane to a concentration of from about 2 to about 5% and the resulting solution is extruded through a nozzle of, for example, a syringe into a bad solvent such as ethanol, methanol, or n-hexane to solidify the resin composition in filamentous configuration.

Since the hydroxyalkanoate polymer composition of the present invention is soluble in a solvent such as chloroform or 1,2-dichloroethane as mentioned above, the solution may be cast into a sheet or a film. The thus produced sheet or film may be produced into a coalescence preventing film.

Furthermore, the hydroxyalkanoate polymer composition of the present invention may be produced into a laminate by dip-coating or roll-coating the solution of the resin composition in the above-mentioned solvent on an appropriate sheet material.

The thus produced medical device of the present invention is sterilized before its use. The sterilization may be carried out by any desired conventional process such as sterilization using an autoclave; sterilization using ionizing radiation such as ultraviolet, γ-ray or electron beam; gas sterilization using such reagent as ethylene oxide; or chemical sterilization using such reagent as an alcohol.

The present invention is hereinafter described in further detail by referring to the following non-limiting Examples of the invention and Comparative Examples.

Crystallization speed of a polymer can be determined by measuring such an index as alteration in specific volume, ultrared crystalline band, degree of X-ray diffraction, broad width NMR spectrum, amount of heat released upon crystallization, and change in degree of depolarization. The crystallization speed described in the present invention is determined by measuring change in the degree of depolarization in accordance with the process described in Kobunshi Kagaku (Polymer Chemistry), vol. 1, No. 29, pp 139–143. This process is based on the principle that the resin composition melted at an elevated temperature is quenched to a constant temperature, and change in double refraction of the resin composition is measured at this constant temperature. The change in double refraction caused in relation to the crystallization is measured as an index of the degree of the crystallinity upon crystallization of resin composition containing the nucleating agent.

EXAMPLE 1 AND COMPARATIVE EXAMPLE 1

A hydroxybutyrate-hydroxyvalerate copolymer having a hydroxyvalerate content of 17% and a molecular weight of about 800,000 was dissolved in chloroform to a polymer content of 5% (w/w). To the solution was added 1% by weight based on the polymer content of an additive as shown in Table 1. The mixture was ultrasonicated to disperse the additive in the solution, and the dispersion was cast onto a glass plate to prepare a sample plate.

The thus produced sample plate was evaluated for its crystallization speed by measuring the degree of depolarization. The results are also shown in Table 1.

It should be noted that the measurement of the depolarization was carried out in a silicone oil at a temperature of 60° C., and the crystallization speed is shown in terms of half time of crystallization, which is the time required for the degree of depolarization to become half of the value at the stage wherein the resin composition had fully undergone its crystallization.

TABLE 1

Effects on crystallization speed of the addition of various amino acids and boron nitride to the resin composition

|  | Additive | Half time of crystallization, min. |
|---|---|---|
| Comparative Example 1 | — | 17.5 |
| Example 1–1 | Boron nitride (average particle size, 3.5 μm) | 1.4 |
| Example 1–2 | Boron nitride (average particle size, 0.6 μm) | 1.1 |
| Example 1–3 | Tyrosine | 1.1 |
| Example 1–4 | Phenylalanine | 2.3 |
| Example 1–5 | Isoleucine | 21.0 |
| Example 1–6 | Taurine | 17.2 |
| Example 1–7 | Phosphoserine | 22.4 |

The results of Table 1 reveal that the aromatic amino acids, and in particular, tyrosine have an excellent nucleating effect equivalent with or superior to that of the boron nitride.

EXAMPLE 2

The procedure of Example 1 was repeated except that tyrosine was added to the hydroxybutyrate-hydroxyvalerate copolymer solution in an amount of not less than 0.1% by weight based on the polymer content to prepare the sample plates.

EXAMPLE 3 AND COMPARATIVE EXAMPLE 2

To a powder of hydroxybutyrate-hydroxyvalerate copolymer having a hydroxyvalerate content of 17% and a molecular weight of about 800,000 was added 0.5% by weight of tyrosine powder, and the mixture was kneaded with rolls at 150° C. to prepare a tyrosine-added polymer. The polymer was melt-pressed at 170° C., and then, pressed at 20° C. for 30 minutes for cooling. The thus produced sheet of 1 mm thick had been uniformly cured to exhibit no distortion.

When the polymer (Comparative Example 2) containing no tyrosine was pressed by repeating the above-described procedure, the polymer underwent an insufficient curing, and the sheet became distorted upon removal of the sheet from the press machine.

It is apparent from the results that addition of the tyrosine results in improved molding properties as well as a shortened molding time of the polymer.

EXAMPLE 4 AND COMPARATIVE EXAMPLE 3

The tyrosine-added polymer and the polymer (Comparative Example 3) containing no tyrosine prepared in Example 3 were respectively compression molded and shaped into standard notched samples adapted for an impact test. The samples were evaluated for their impact strength by Izot impact test for hard plastics according to JIS K 7110. The results are shown below:

|  | Nucleating agent | Izot impact strength, J/m |
|---|---|---|
| C. Ex. 3 | — | 130 |
| Ex. 4 | 0.5% tyrosine | 263 |

The results reveal that the test sample prepared from the tyrosine-added polymer has an improved impact strength as well as a reduced brittleness.

The sample plates were evaluated for their crystallization speed by measuring the degree of depolarization. The results are shown in FIG. 1, wherein the half time of crystallization is plotted in relation to the tyrosine content in part by weight based on 100 parts by weight of the hydroxybutyrate-hydroxyvalerate copolymer to show the dependency of the crystallization speed on the tyrosine content. The results shown in FIG. 1 reveal that an addition of tyrosine at a content of 0.1% by weight or more should result in a significant increase in the crystallization speed.

EFFECTS OF THE INVENTION

As described above, addition to the hydroxyalkanoate polymer of 0.1% by weight or more of an aromatic amino acid as a nucleating agent based on the polymer content should result in a significant increase in the crystallization speed of the resulting resin composition. Such an increase in the crystallization speed should realize various improvements in the properties of the molded article including an increased non-brittleness. At the same time, articles fabricated by using such a resin composition is capable of undergoing a safe decomposition in a living body.

I claim:

1. A resin composition comprising
   100 parts by weight of a hydroxyalkanoate polymer, and
   0.1 to 10 parts by weight of an aromatic amino acid which acts as a crystallization nucleating agent.

2. The resin composition according to claim 1 wherein the hydroxyalkanoate polymer is a polymer having weight average molecular weight of 1,000–1,000,000 represented by the recurring unit of the formula (I):
wherein R is hydrogen or an alkyl group having 1 to 4 carbon atoms; n is an integer of from 1 to 8.

3. The resin composition according to claim 2 wherein said hydroxyalkanoate polymer is a homopolymer or copolymer of at least one repeated structural unit selected from the group consisting of hydroxybutyrate unit wherein R is methyl and n is 1; and hydroxyvalerate unit wherein R is ethyl and n is 1.

4. The resin composition according to claim 3 wherein the amount of the hydroxyvalerate of said copolymer is from 0 to 30% (w/w).

5. The resin composition according to claim 1 wherein said crystallization nucleating agent is at least one member selected from the group consisting of tyrosine and phenylalanine.

6. A medical device fabricated by using the resin composition of claim 1.

7. The medical device according to claim 6 wherein said device is at least one member selected from the group consisting of infusion system, blood transfusion system, blood circuit, catheter, blood bag, infusion bag, dialysis bag, perintestinal nutrient bag, suture, mesh, patch, pledget, prosthesis, staple, clip, coalescence preventing film, and implant material and screw used for its fixing.

8. A medical device constituted of a resin composition according to claim 5.

9. The medical device according to claim 8 wherein said device is selected from the group consisting of an infusion system, blood transfusion system, blood circuit, catheter blood bag, infusion bag, dialysis bag, perintestinal nutrient bag, suture, mesh, patch, pledger, prosthesis, clip, coalescence preventing film, implant material and screw used for its fixing.

* * * * *

UNITED STATES PATENT AND TRADEMARK OFFICE
CERTIFICATE OF CORRECTION

PATENT NO. : 5,516,565
DATED : May 14, 1996
INVENTOR(S) : Atsushi MATSUMOTO

It is certified that error appears in the above-indentified patent and that said Letters Patent is hereby corrected as shown below:

In Column 3, line 61, delete "hydroxyatkanoate" and insert -- hydroxyalkanoate --.

In Column 8, line 61, after "(I):", insert

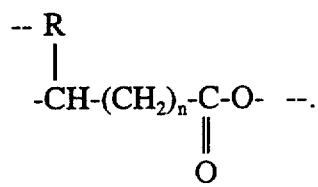

--.

Signed and Sealed this

Twenty-fourth Day of September, 1996

Attest:

BRUCE LEHMAN

Attesting Officer    Commissioner of Patents and Trademarks